(12) United States Patent
Montaldo et al.

(10) Patent No.: US 9,140,781 B2
(45) Date of Patent: Sep. 22, 2015

(54) IMAGING METHOD AND APPARATUS USING SHEAR WAVES

(75) Inventors: Gabriel Montaldo, Paris (FR); Jeremy Bercoff, Aix-en-Provence (FR); Mickael Tanter, Bagneux (FR); Mathias A. Fink, Meudon (FR)

(73) Assignees: SUPER SONIC IMAGINE, Aix-en-Provence (FR); CENTRE NATIONAL DE LA RECHERCHE SCIENTIFIQUE (CNRS), Paris (FR); UNIVERSITE PARIS DIDEROT-PARIS 7, Paris (FR)

( * ) Notice: Subject to any disclaimer, the term of this patent is extended or adjusted under 35 U.S.C. 154(b) by 301 days.

(21) Appl. No.: 13/642,478

(22) PCT Filed: Apr. 20, 2010

(86) PCT No.: PCT/IB2010/001282
§ 371 (c)(1),
(2), (4) Date: Oct. 19, 2012

(87) PCT Pub. No.: WO2011/132014
PCT Pub. Date: Oct. 27, 2011

(65) Prior Publication Data
US 2013/0031981 A1 Feb. 7, 2013

(51) Int. Cl.
*G01N 29/04* (2006.01)
*G01S 7/52* (2006.01)
*A61B 8/08* (2006.01)

(52) U.S. Cl.
CPC .............. *G01S 7/52036* (2013.01); *A61B 8/485* (2013.01); *G01S 7/52042* (2013.01); *G01S 7/52046* (2013.01); *G01S 7/52065* (2013.01); *G01S 7/52071* (2013.01); *G01S 7/52077* (2013.01)

(58) Field of Classification Search
CPC ............ G01S 7/52036; G01S 7/52071; G01S 7/52065; G01S 7/52042; G01S 7/52077; A61B 8/465
USPC ............. 73/606, 597, 602, 626; 600/443, 447
See application file for complete search history.

(56) References Cited

U.S. PATENT DOCUMENTS 6,770,033 B1    8/2004  Fink et al.
7,175,599 B2 *  2/2007  Hynynen et al. .............. 600/443
(Continued)

FOREIGN PATENT DOCUMENTS

CN         1809317 A      7/2006
CN       201370595 Y     12/2009
(Continued)

OTHER PUBLICATIONS

Bercoff, J., et al., "Supersonic Shear Imaging: A New Technique for Soft Tissue Elasticity Mapping," IEEE Transactions on Ultrasonics, Ferroelectrics and Frequency Control, IEEE, vol. 51, No. 4, Apr. 2004.
(Continued)

*Primary Examiner* — J M Saint Surin
(74) *Attorney, Agent, or Firm* — Marshall, Gerstein & Borun LLP (57) ABSTRACT

An imaging method using shear waves for observing a viscoelastic medium, comprising:
several successive excitation steps j during which elastic shear waves are generated respectively at different excitation loci ($L_j$) in the viscoelastic medium by an imaging device, the different excitation loci being separated from one another by a maximum distance Dm,
an imaging step corresponding to each excitation step j, in which a set j of successive raw images $Imj(tk)$ of the viscoelastic medium at times tk are determined during propagation of the shear wave, the raw images having a resolution R which is larger than the maximum distance Dm,
an averaging step in which raw images $Imj(tk)$ corresponding to the same relative time tk are averaged to determine an average image $Im'(tk)$.

19 Claims, 4 Drawing Sheets

(56) References Cited

U.S. PATENT DOCUMENTS

| | | | |
|---|---|---|---|
| 7,252,004 | B2 | 8/2007 | Fink et al. |
| 7,444,875 | B1 | 11/2008 | Wu et al. |
| 8,147,410 | B2 * | 4/2012 | Zheng .................. 600/438 |
| 8,187,187 | B2 * | 5/2012 | Fan et al. ............... 600/438 |
| 8,419,642 | B2 | 4/2013 | Sandrin et al. |
| 8,545,407 | B2 * | 10/2013 | Bercoff et al. ......... 600/438 |
| 8,726,734 | B1 * | 5/2014 | Lin ........................ 73/626 |
| 2005/0165307 | A1 | 7/2005 | Nishigaki et al. |
| 2010/0170342 | A1 | 7/2010 | Sinkus et al. |

FOREIGN PATENT DOCUMENTS

| | | |
|---|---|---|
| CN | 101657159 A | 2/2010 |
| CN | 101690677 A | 4/2010 |
| FR | 2 791 136 | 9/2000 |
| JP | 2002-538911 A | 11/2002 |
| JP | 2003-530941 A | 10/2003 |
| JP | 2009-534198 A | 9/2009 |
| WO | WO-2008/139245 A1 | 11/2008 |
| WO | WO-2009/007582 A2 | 1/2009 |
| WO | WO-2010/012092 A1 | 2/2010 |

OTHER PUBLICATIONS

Couade, M., et al., "Non-invasive quantitative imaging of arterial wall elasticity using supersonic shear imaging," IEEE Ultrasonics Symposium, IEEE, pp. 946-949, 2008.

Montaldo, G. Et al., "Coherent plane-wave compounding for very high frame rate ultrasonography and transient elastography," IEEE Transactions on Ultrasonics, Ferroelectrics and Frequency Control, IEEE, vol. 56, No. 3, Mar. 2009.

Szabo, Thomas L., "Casual theories and data for acoustic attenuation obeying a frequency power law," J. Acoust. Soc. Am. 97 (1), 1995.

Tourin et al., "Multiple scattering of sound, Waves in Random Media," 10:4, R31-R60, 2000.

International Search Report for PCT/IB2010/001282, mailed Jan. 21, 2011.

Search Report for Chinese Patent Application No. 2010800676974, Jan. 26, 2014.

\* cited by examiner

IMAGING METHOD AND APPARATUS USING SHEAR WAVES

FIELD OF THE INVENTION

The present invention relates to imaging methods and apparatuses using shear waves.

BACKGROUND OF THE INVENTION

More particularly, the invention relates to an imaging method using shear waves for observing a viscoelastic medium, comprising:
- an excitation steps j during which elastic shear waves are generated at an excitation locus in the viscoelastic medium by an imaging device,
- an imaging step in which a set of successive images of the viscoelastic medium are determined by said imaging device during propagation of the shear wave in said viscoelastic medium.

Document U.S. Pat. No. 7,252,004 describes an example of such a method, in which the successive images, constituting a motion picture of the propagation of the shear wave, are used to map the viscoelastic medium, by calculating at least one propagation parameter of the shear wave at one or several points in the viscoelastic medium.

Although this known method gives particularly good results, e.g. for spotting cancerous zones or the like, such method may produce images having a relatively low signal-to-noise ratio in certain circumstances, for instance in biological mediums having very complex structures producing high attenuation and diffraction (e.g. animal muscle when the shear waves are propagated transversely to muscle fibers).

OBJECTS OF THE INVENTION

A particular object of the present invention is to mitigate this drawback.

To this end, the invention proposes an imaging method using shear waves for observing a viscoelastic medium, comprising:
- several successive excitation steps j during which elastic shear waves are generated respectively at different excitation loci in the viscoelastic medium by an imaging device, said different excitation loci being separated from one another by a maximum distance Dm,
- an imaging step corresponding to each excitation step j, in which a set j of successive raw images $Im_j(t_k)$ of the viscoelastic medium at times $t_k$ are determined by said imaging device during propagation of the shear wave in said viscoelastic medium, said raw images having a resolution R which is at least equal to said maximum distance Dm, $t_k$ being a relative time counted from generation of the corresponding shear wave,
- an averaging step in which raw images $Im_j(t_k)$ corresponding to the same relative time $t_k$ are averaged to determine an average image $Im'(t_k)$ corresponding to said relative time $t_k$.

Thus, the invention enables to eliminate most of the noise in the raw images, and enables to obtain averaged images having a higher signal-to-noise ratio. Therefore, the averaged images can be more efficiently treated to obtain a better mapping of a shear wave propagation parameter, and optionally to obtain a spectroscopy of said propagation parameter (i.e. values of said propagation parameter as a function of the frequency) which enable to obtain certain rheological values of the viscoelastic medium and in particular the rheological values representing viscous effects.

In various implementations of the method of the invention, it is optionally possible also to have recourse to one or more of the following dispositions:
- the method further comprises, between the imaging step and the averaging step, a repositioning step in which the raw images $Im_j(t_k)$ are spatially repositioned so that the different excitation loci are positioned in mutual correspondence in the raw images $Im_j(t_k)$;
- said raw images $Im_j(t_k)$ are spatially repositioned by offsetting a coordinate system of each raw image so that the different excitation loci have the same coordinates in the raw images $Im_j(t_k)$;
- a number J of said sets j of successive raw images, is at least 5;
- each excitation locus is separated from adjacent excitation loci by a pitch which is at most R/5, and which preferably is at most R/10;
- the excitation locus is moved in the viscoelastic medium by the imaging device from one excitation step to the other;
- the viscoelastic medium is moved while the excitation locus remains fixed relative to the imaging device from one excitation step to the other, so that the excitation locus is moved in the viscoelastic medium from one excitation step to the other;
- said shear excitation is generated by at least one ultrasound wave emitted into the viscoelastic medium by an array of ultrasound transducers belonging to said imaging device;
- said shear excitation is generated by applying an outside mechanical force to the viscoelastic medium at each excitation locus;
- each raw image $Im_j(t_k)$ is obtained either by ultrasound imaging, or by IRM;
- the method comprises a characterizing step during which, based on said average images $Im'(t_k)$ over time, at least one shear wave propagation parameter is calculated at at least one point of the viscoelastic medium;
- the shear wave propagation parameter which is calculated during the characterizing step, is selected from shear wave speed, shear modulus, Young's modulus, shear wave attenuation, shear elasticity, shear viscosity, mechanical relaxation time and anisotropy;
- said excitation has a bandwidth of at least 500 Hz and said shear wave propagation parameter is calculated at a plurality of frequencies in said bandwidth.

Furthermore, the invention also provides an imaging apparatus for implementing a method according to any preceding claim using shear waves to observe a viscoelastic medium, said apparatus comprising at least one electronic central unit adapted:
- to generate elastic shear waves respectively at different excitation loci in the viscoelastic medium during several successive excitation steps j, said different excitation loci being separated from one another by a maximum distance Dm,
- to determine a set j of successive raw images $Im_j(t_k)$ of the viscoelastic medium at times $t_k$ during propagation of the shear wave in said viscoelastic medium respectively for each excitation step j, said raw images having a resolution R which is at least equal to said maximum distance Dm, $t_k$ being a relative time counted from generation of the corresponding shear wave,
- to average raw images $Im_j(t_k)$ corresponding to the same relative time $t_k$ for determining an average image $Im'(t_k)$ for said relative time $t_k$.

In various implementations of the apparatus of the invention, it is optionally possible also to have recourse to one or more of the following dispositions:

said electronic central unit is further adapted to spatially reposition said raw images $Im_j(t_k)$ before averaging said images so that the different excitation loci are positioned in mutual correspondence in the raw images $Im_j(t_k)$;

said electronic central unit is adapted to spatially reposition said raw images $Im_j(t_k)$ by offsetting a coordinate system of each raw image so that the different excitation loci have the same coordinates in the raw images $Im_j(t_k)$;

said electronic central unit is adapted to move the excitation locus in the viscoelastic medium from one excitation step to the other;

said electronic central unit is adapted to calculate at least one shear wave propagation parameter at at least one point of the viscoelastic medium based on successive average images over time, said shear wave propagation parameter being selected from shear wave speed, shear modulus, Young's modulus, shear wave attenuation, shear elasticity, shear viscosity, mechanical relaxation time and anisotropy;

said apparatus is adapted to apply said with a bandwidth of at least 500 Hz and said electronic central unit is adapted to calculate said shear wave propagation parameter at a plurality of frequencies in said bandwidth.

Other characteristics and advantages of the invention appear from the following description of an embodiment thereof, given by way of non-limiting example and with reference to the accompanying drawing.

MORE DETAILED DESCRIPTION

In the various figures, like references designate elements that are identical or similar.

Figure 1:
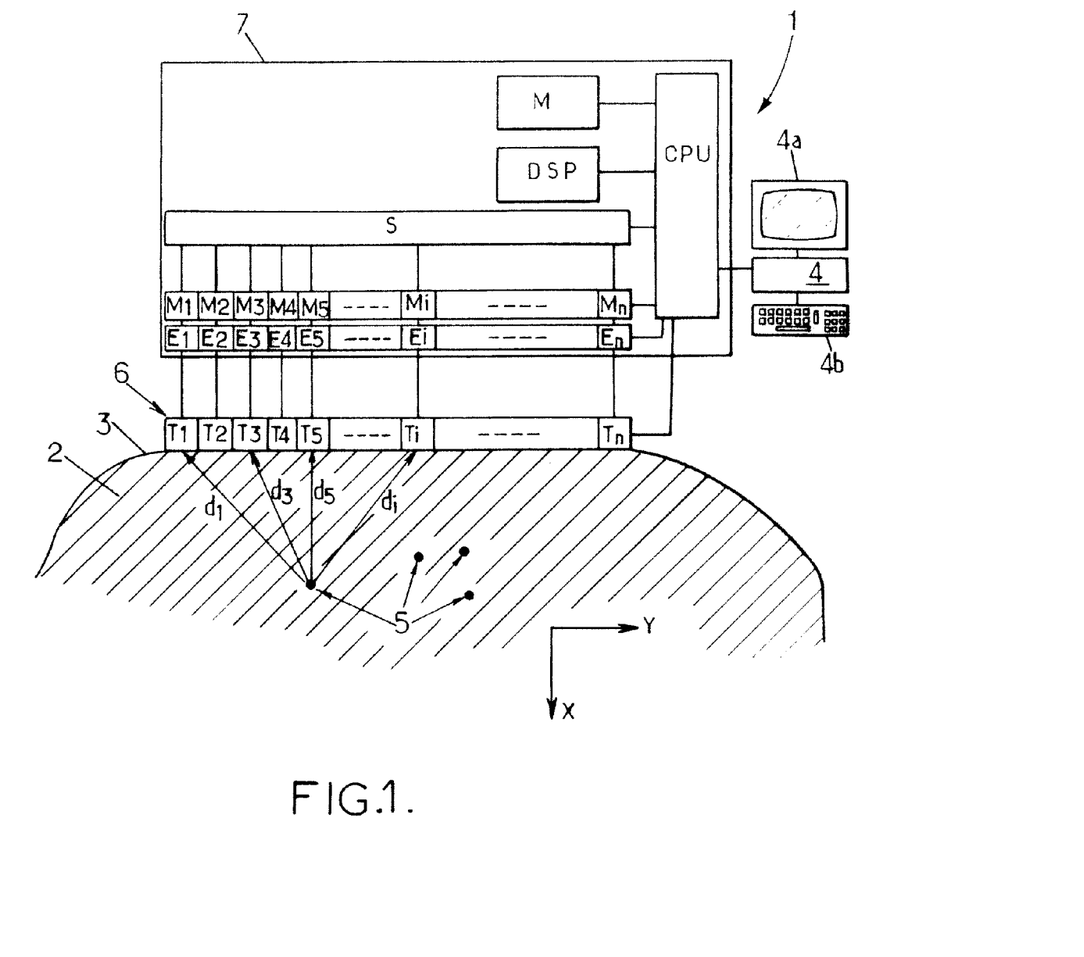
FIG. 1 is a diagrammatic view of an example of a shear-wave imaging device in one embodiment of the invention.

The imaging device 1 shown in FIG. 1 is for studying the propagation of elastic shear waves in a viscoelastic medium 2 that diffuses ultrasound waves in compression, and that may be constituted, for example:

by an inert body, in particular for quality control in industrial applications; or a living body, for example a portion of the body of a patient, in medical applications.

By way of example, these movements are tracked by means of a microcomputer 4 (comprising at least an input interface 4b such as a keyboard, etc., and an output interface 4a such as a screen, etc.) or any other electronic central unit, serving to send ultrasound compression waves into the medium 2 from its outside surface 3. These compression waves interact with diffusing particles 5 contained in the medium 2, which particles are reflective for ultrasound compression waves. The particles 5 may be constituted by any non-uniformity in the medium 2, and in particular, in a medical application, they may be constituted by particles of collagen present in human tissues (in echographic images, such particles form points known as "speckle").

To observe the propagation of the shear wave, an ultrasound probe 6 is used that is disposed against the outside surface 3 of the observed medium 2. This probe delivers ultrasound compression wave pulses along an axis X, which pulses are of the type commonly used in echography, for example having a frequency lying in the range 0.5 MHz to 100 MHz, and preferably in the range 0.5 MHz to 15 MHz, e.g. being about 4 MHz.

The ultrasound probe 6 is constituted by an array of n ultrasound transducers $T_1, T_2, \ldots T_i, \ldots T_n$, where n is an integer not less than 1. By way of example, the probe 6 may be in the form of a linear strip of transducers comprising, for example, n=128 transducers in alignment along an axis Y that is perpendicular to the axis X. However, the probe in question could equally be in the form of a two-dimensional array of transducers (plane or otherwise).

The transducers $T_1$-$T_n$ are controlled independently of one another by the microcomputer 4, possibly via a central unit CPU which is contained for example in an electronic rack 7 connected via a flexible cable to the probe 6. The transducers T1-Tn can thus emit selectively:

either an ultrasound compression wave that is "plane" (i.e. a wave whose wave front is rectilinear in the X,Y plane), or any other type of focused or unfocused wave illuminating the entire observation field in the medium 2, for example a wave generated by causing random sound signals to be emitted by the various transducers $T_1$-$T_n$;

or else an ultrasound compression wave that is focused on one or more points of the medium 2.

To observe the propagation of the shear wave in the medium 2, several steps are performed in succession:

a) an excitation step during which the microcomputer causes an elastic shear wave to be generated in the viscoelastic medium 2 by causing at least one ultrasound wave that is focused in the viscoelastic medium to be emitted by the probe 6;

b) an observation step during which the propagation of the shear wave is observed simultaneously at a multitude of observation field points in the viscoelastic medium 2, c) and an imaging step during which the microcomputer 4 processes the sound signals received from the viscoelastic medium 2 during substep b2) in order to determine successive propagation images at successive instants $t_k$ ($t_k$ may be relative times, counted from the generation of the shear wave).

a) Excitation Step

During the excitation step a), the shear excitation can be created by at least one focused ultrasound wave emitted into the viscoelastic medium 2 by the array of ultrasound transducers 6.

The focused ultrasound wave emitted during the excitation step a) may be a monochromatic wave of frequency f lying in the range 0.5 MHz to 15 MHz, for example being equal to about 4 MHz, which is emitted for a duration of p/f seconds, where p is an integer lying in the range 50 to 5000 (e.g. being about 500) and f is expressed in Hz. Such excitation in the form of a rectangular signal or similar, may produce a shear wave with a relatively large bandwidth of at least 500 Hz (for instance a bandwidth of 0-1000 Hz).

The focused ultrasound wave emitted during excitation step a) may be focused on a single focus point or on a plurality of focus points so that the shear wave as generated presents a desired wave shape and illuminates desired zones in the medium 2. The focus point(s) constitute the excitation locus, where the shear wave is generated. For example, the excitation locus L may be in the form of a straight line obtained by quickly focusing several successive ultrasound waves along this straight line, in which case it is possible to generate a shear wave that is plane as explained for instance by Bercoff et al. ["Supersonic Shear Imaging: a New Technique for Soft Tissue Elasticity Mapping", IEEE transactions on ultrasonics, ferroelectrics, and frequency control, vol. 51, no. 4, April 2004, p. 396-409].

b) Observation Step

The observation step may comprise the following substeps:

b1) the microcomputer 4 causes the probe 6 to emit into the viscoelastic medium a succession of ultrasound compression wave shocks, which may preferably be unfocussed or lightly focused, at a rate of at least 500 shots per second [the focusing and the timing of the focus ultrasound wave emitted in step a), and the timing of said ultrasound waves are adapted so that at least some of said ultrasound waves reach the observation field during the propagation of the shear wave through the observation field, for at least some of the ultrasound wave emissions];

b2) the microcomputer 4 causes the probe 6 to detect and record in real time sound signals received from the viscoelastic medium 2, said signals comprising echoes generated by the ultrasound compression wave interacting with the reflecting particles 5 in the viscoelastic medium, these echoes corresponding (directly or indirectly) to successive images of the displacement of the viscoelastic medium.

During step b1), which may last for example for less than one second, it is possible to emit for instance unfocused ultrasound compression waves at a rate lying in the range 500 to 10,000 shots per second, and preferably in the range 1000 to 5000 shots per second (with this rate being limited by the go-and-return travel time for the compression wave through the medium 2, i.e. by the thickness of the medium 2 in the direction X: it is necessary for all of the echoes that are generated by the compression wave to have been received by the probe 6 before a new compression wave is sent).

Each unfocused ultrasound compression wave propagates through the medium 2 at a propagation speed that is much higher than that of shear waves (e.g. about 1500 meters per second (m/s) in the human body), and interacts with the reflecting particles 5, thereby generating echoes or other analogous disturbances in the signal that are known in themselves under the name "speckle noise" in the field of echography.

The speckle noise is picked up by the transducers $T_1$-$T_n$ during substep b2), after each shot k of an unfocused ultrasound compression wave. The signal $s_i(t_k)$ as picked up in this way by each transducer Ti after shot No. k is initially sampled at high frequency (e.g. 30 MHz to 100 MHz) and is digitized in real time (e.g. on 12 bits) by a sampler forming part of the rack 7 and connected to said transducer, the samplers being referenced respectively $E_1, E_2, \ldots, E_n$.

The signal $s_i(t_k)$ as sampled and digitized in this way is then stored, likewise in real time, in a memory $M_i$ belonging to the rack 7 and specific to the transducer $T_i$.

By way of example, each memory $M_i$ presents a capacity of about 128 megabytes (MB), and contains all of the signals $s_i(t_k)$ received in succession for shots k=1 to q where q is the total number of ultrasound shots.

c) Imaging Step

The imaging step c) can be performed by microcomputer 4 for instance in deferred time, after all of the signals $s_i(t_k)$ corresponding to the same propagation of a shear wave have been stored, the central unit CPU causes these signals to be reprocessed by a summing circuit S belonging to the rack 7 (or else it performs this treatment itself, or indeed the treatment may be performed in the microcomputer 4), using a conventional path-forming step corresponding to substep c1), as explained for instance in U.S. Pat. No. 7,252,004.

This generates images Im($t_k$), e.g. 2D images in the present case, each in the form of a matrix corresponding to discrete positions of coordinates (x,y) in the observation field, each corresponding to the image of the observation field after shot No. k.

After the path-forming step, the central unit CPU stores the images Im($t_k$) in a central memory M forming part of the rack 7 or in the microcomputer 4.

Each image Im($t_k$) may have a resolution R of around 1 mm or less.

Reiteration of Steps a-c

According to the present invention, steps a-c are reiterated for a number of times J which can be for instance comprised between 4 and 10. During the excitation steps j=1 to J, the excitation locus $L_j$ is offset from one iteration j to the other by the imaging device 1 (by changing the focusing of the ultrasound waves transmitted by the transducer array 6, i.e. by changing the delays applied to the transducers $T_1$-$T_n$, as it is well known in the art). The successive excitation loci $L_j$ are separated from one another by a maximum distance Dm which is at most equal to, preferably lower than, said resolution R. In a particular embodiment, each excitation locus $L_j$ can be separated from adjacent excitation loci by a pitch which is at most R/5, and which preferably is at most R/10. For instance, one may use J=7 iterations and the excitation loci $L_j$ may be offset of a pitch of R/10 at each iteration, so that the total offset Dm between the first iteration (j=1) to the last (j=J) is equal to 7R/10.

Figure 2:
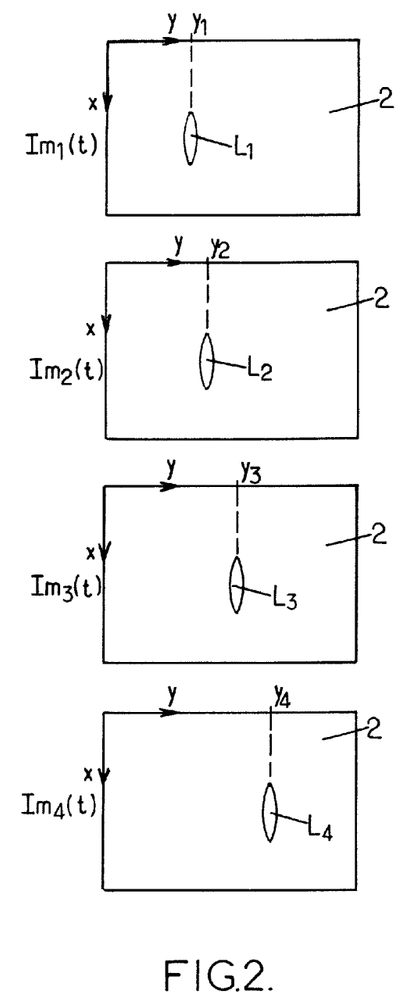
FIG. 2 illustrates an example of a set of successive raw images of the viscoelastic medium, determined by the imaging device of FIG. 1, showing the excitation loci at which the shear waves are successively generated in the viscoelastic medium.

When the excitation locus $L_j$ is a straight line parallel to axis X as shown for instance on FIG. 2, said excitation locus $L_j$ can be offset of said pitch parallel to axis Y from one iteration to the following. The above offset can be obtained by the fact that the excitation locus $L_j$ is moved in the viscoelastic medium 2 by the imaging device 1 from one excitation step a) to the other. When the excitation locus is a straight line, this line can also be offset from one iteration to the other by tilting this line of a small angle (a few degrees): in this case, the distance from each point of one excitation line to another excitation line (said distance is then measured perpendicularly to the excitation line where said point belongs) varies along said line and said maximum distance Dm is the maximum value of said distance from one point of one excitation locus to the other excitation locus.

In a variant, the viscoelastic medium 2 is moved from one excitation step to the other while the array 6 remains fixed and the excitation locus remains fixed relative to the transducer array 6, so that the excitation locus $L_j$ is moved in the viscoelastic medium 2 from one excitation step to the other. This may apply for instance when the medium 2 is part of the heart or of the liver of a living human or animal. In such a case, the successive excitation steps a) may be carried out at times where the position of the medium 2 is very close to a reference position, so that the maximum distance Dm between the excitation loci remains less than the resolution R.

After each excitation step j, one obtains a set of images $Im_j(t_k)$ as explained above, at successive instants $t_k$. These images $Im_j(t_k)$ will be called raw images hereafter.

d) Repositioning Step

Figure 3:
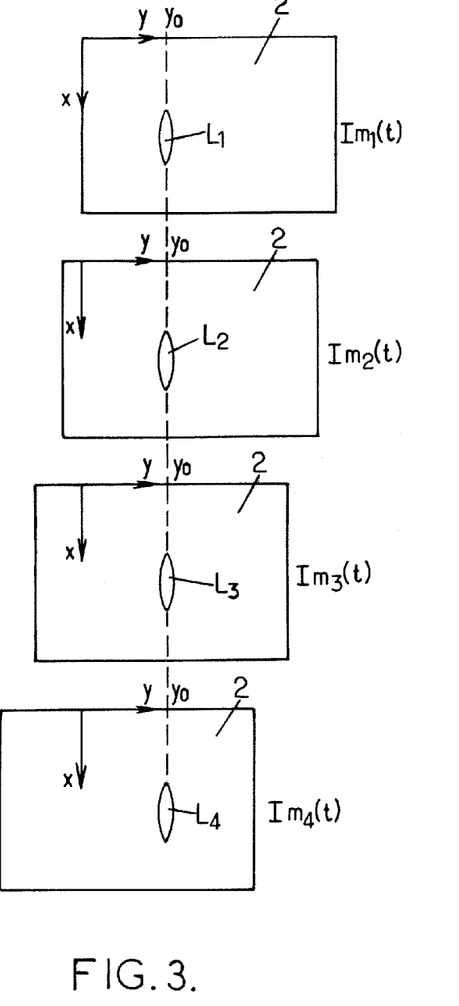
FIG. 3 illustrates a repositioning step in which the raw images are spatially repositioned so that the different excitation loci are positioned in mutual correspondence in the raw images.

As shown on FIG. 3, the raw images $Im_j(t_k)$ may be spatially repositioned so that the different excitation loci ($L_j$) are positioned in mutual correspondence in the various raw images $Im_j(t_k)$. This repositioning can be obtained for instance by offsetting the coordinate system (x, y) [or a 3D coordinate system (x,y,z) in case of a 3D imaging] of the raw images $Im_j(t_k)$ so that the different excitation loci ($L_j$) have the same coordinates in all the raw images $Im_j(t_k)$. The repositioning step can be carried out either on each raw image after each imaging step c), or on all raw images at the same time after all iterations of steps a-c.

This repositioning step may optionally be omitted. When the viscoelastic medium 2 is movable and the excitation locus remains fixed relative to the transducer array as explained above, this repositioning step can be preferably omitted; on the contrary, when the excitation locus $L_j$ is moved relative to the transducer array from one iteration to the other, said repositioning is preferably used.

e) Averaging Step

The raw images $Im_j(t_k)$ (after their repositioning if any) corresponding to the same relative time $t_k$ are then averaged to determine an average image $Im'(t_k)$ corresponding to said relative time $t_k$. The average can be a simple arithmetic average of the pixel values $s_j(t_k)(x,y)$ of the raw images.

Figure 4:
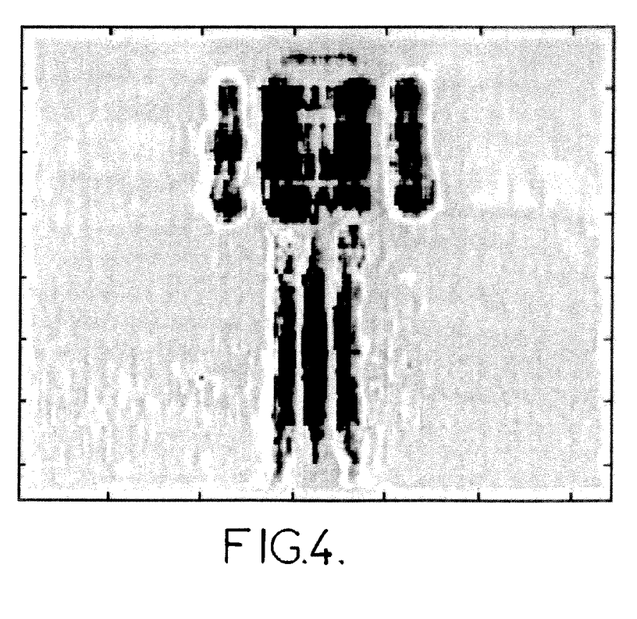
FIG. 4 is an example of an average image obtained by averaging the various repositioned raw images of FIG. 3, in a particular example.
Figure 5:
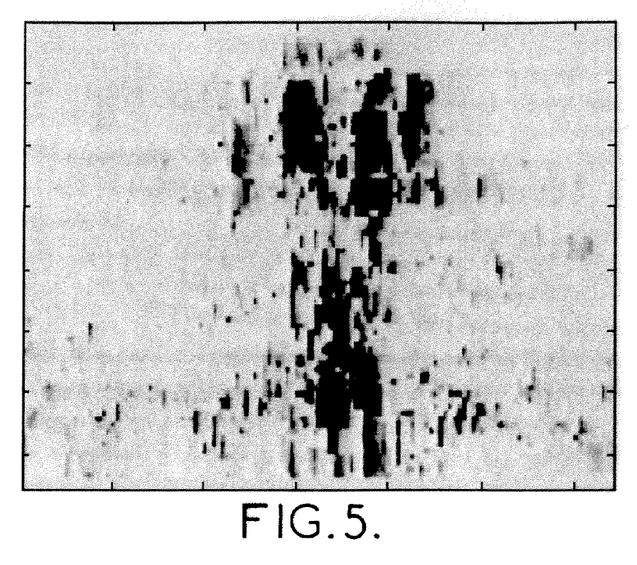
FIG. 5 is a raw image corresponding to the average image of FIG. 4.

As shown on FIG. 4, the averaging step enables to obtain an average image of much better quality than the raw images as that shown on FIG. 5. In particular, the signal-to-noise ratio of the image is dramatically increased by the averaging step, which enables better characterization of the rheological features of the viscoelastic medium 2 at the next step.

At 2 mm lateral distance from the pushing area, the maximum shear wave frequency is 200 Hz (@-6 dB). All frequency components above 200 Hz have been attenuated by the tissue. When using the new averaging method, the maximum shear wave frequency is 500 Hz (@-6 dB) giving access, for a given location, to much more information about tissue viscoelasticity than in the conventional method.

f) Characterizing Step

Based on the average images $Im'(t_k)$ over time, at least one shear wave propagation parameter is calculated at at least one point of the viscoelastic medium, preferably on the complete image to obtain a mapping of the viscoelastic medium. This shear wave propagation parameter can be selected for instance from shear wave speed, shear modulus, Young's modulus, shear wave attenuation, shear elasticity, shear viscosity, mechanical relaxation time and anisotropy. Such parameter can be determined for instance as explained in U.S. Pat. No. 7,252,004

Further, due to the good signal-to-noise ratio of the averaged images, it is possible to carry out a spectrometric analysis of said parameter. For instance, as shown on FIG. 6, when said parameter is the speed v of the shear waves, it is possible to determine said speed v as a function of the frequency f in the bandwidth of the shear wave.

Figure 6:
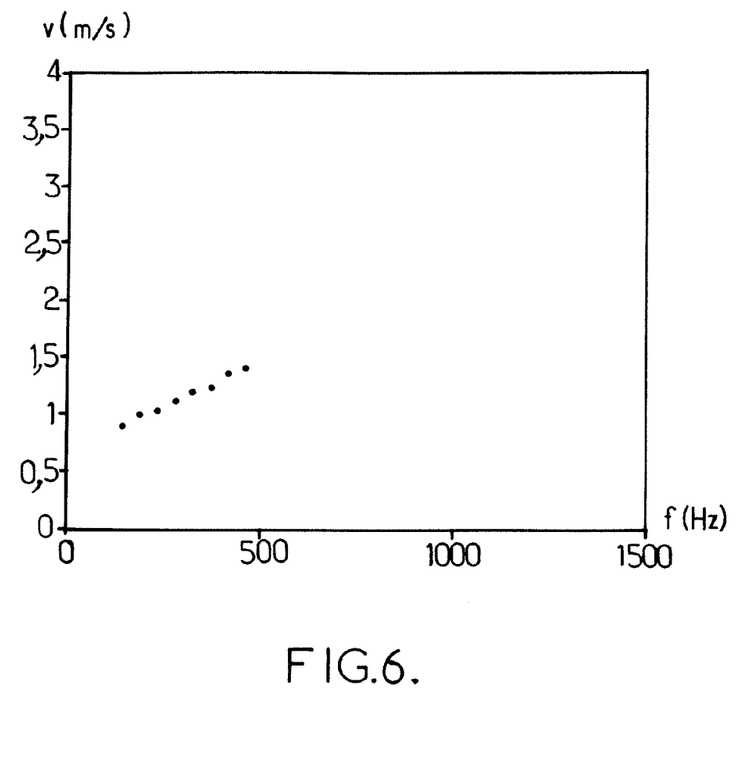
FIG. 6 is a diagram showing the shear wave speed as a function of the frequency, computed at one point of the viscoelastic medium from successive averaged images such as that of FIG. 4.

When the measured parameter is shear wave attenuation $\alpha$, such attenuation may be considered as varying according to a law such as (see for instance:

$$\alpha(f) = \alpha_0 + \alpha_1 f^a$$

where f is the shear wave frequency and $a$ is a power factor generally comprised between 0 and 2 for mechanical waves in biological mediums. In this case, the present invention can enable to assess the power factor $a$ precisely and to map y in the viscoelastic medium as taught for instance in WO-A-2009/007582.

Variants

In a variant, the excitation of the shear waves could be obtained by applying an outside mechanical force to the viscoelastic medium at each excitation locus, for instance thorough a vibrator controlled by the microcomputer 4, as explained for instance in WO-A-00/55616.

In another variant, each raw image $Im_j(t_k)$ is obtained by IRM rather than by ultrasound imaging.

The invention claimed is:

1. An imaging method using shear waves for observing a viscoelastic medium, comprising:
   several successive excitation steps j during which elastic shear waves are generated respectively at different excitation loci in the viscoelastic medium by an imaging device, said different excitation loci being separated from one another by a maximum distance Dm,
   an imaging step corresponding to each excitation step j, in which a set j of successive raw images $Im_j(t_k)$ of the viscoelastic medium at times $t_k$ are determined by said imaging device during propagation of the shear wave in said viscoelastic medium, said raw images having a resolution R which is at least equal to said maximum distance Dm, $t_k$ being a relative time counted from generation of the corresponding shear wave,
   an averaging step in which raw images $Im_j(t_k)$ corresponding to the same relative time $t_k$ are averaged to determine an average image $Im'(t_k)$ corresponding to said relative time $t_k$.

2. The imaging method according to claim 1, further comprising, between the imaging step and the averaging step, a repositioning step in which the raw images $Im_j(t_k)$ are spatially repositioned so that the different excitation loci are positioned in mutual correspondence in the raw images $Im_j(t_k)$.

3. The imaging method according to claim 2, wherein said raw images $Im_j(t_k)$ are spatially repositioned by offsetting a coordinate system of each raw image so that the different excitation loci have the same coordinates in the raw images $Im_j(t_k)$.

4. The imaging method according to claim 1, wherein a number J of said sets j of successive raw images, is at least 5.

5. The imaging method according to claim 1, wherein each excitation locus is separated from adjacent excitation loci by a pitch which is at most R/5, and which preferably is at most R/10.

6. The imaging method according to claim 1, wherein the excitation locus is moved in the viscoelastic medium by the imaging device from one excitation step to the other.

7. The imaging method according to claim 1, wherein the viscoelastic medium is moved while the excitation locus remains fixed relative to the imaging device from one excitation step to the other, so that the excitation locus is moved in the viscoelastic medium from one excitation step to the other.

8. The imaging method according to claim 1, wherein said shear excitation is generated by at least one ultrasound wave emitted into the viscoelastic medium by an array of ultrasound transducers belonging to said imaging device.

9. The imaging method according to claim 1, wherein said shear excitation is generated by applying an outside mechanical force to the viscoelastic medium at each excitation locus.

10. The imaging method according to claim 1, wherein each raw image $Im_j(t_k)$ is obtained either by ultrasound imaging, or by IRM.

11. The imaging method according to claim 1, comprising a characterizing step during which, based on said average images $Im'(t_k)$ over time, at least one shear wave propagation parameter is calculated at at least one point of the viscoelastic medium.

12. The imaging method according to claim 11, wherein the shear wave propagation parameter which is calculated during the characterizing step, is selected from shear wave speed, shear modulus, Young's modulus, shear wave attenuation, shear elasticity, shear viscosity, mechanical relaxation time and anisotropy.

13. The imaging method according to claim 10, wherein said excitation has a bandwidth of at least 500 Hz and said shear wave propagation parameter is calculated at a plurality of frequencies in said bandwidth.

14. An imaging apparatus for implementing a method according to claim 1 using shear waves to observe a viscoelastic medium, said apparatus comprising at least one electronic central unit adapted:
to generate elastic shear waves respectively at different excitation loci in the viscoelastic medium (2) during several successive excitation steps j, said different excitation loci being separated from one another by a maximum distance Dm,
to determine a set j of successive raw images $Im_j(t_k)$ of the viscoelastic medium at times $t_k$ during propagation of the shear wave in said viscoelastic medium respectively for each excitation step j, said raw images having a resolution R which is at least equal to said maximum distance Dm, $t_k$ being a relative time counted from generation of the corresponding shear wave,
to average raw images $Im_j(t_k)$ corresponding to the same relative time $t_k$ for determining an average image $Im'(t_k)$ for said relative time $t_k$.

15. The imaging apparatus according to claim 14, wherein said electronic central unit is further adapted to spatially reposition said raw images $Im_j(t_k)$ before averaging said images so that the different excitation loci are positioned in mutual correspondence in the raw images $Im_j(t_k)$.

16. The imaging apparatus according to claim 15, wherein said electronic central unit is adapted to spatially reposition said raw images $Im_j(t_k)$ by offsetting a coordinate system of each raw image so that the different excitation loci have the same coordinates in the raw images $Im_j(t_k)$.

17. The imaging apparatus method according to claim 14, wherein said electronic central unit is adapted to move the excitation locus in the viscoelastic medium from one excitation step to the other.

18. The imaging apparatus according to claim 14, wherein said electronic central unit is adapted to calculate at least one shear wave propagation parameter at at least one point of the viscoelastic medium based on successive average images over time, said shear wave propagation parameter being selected from shear wave speed, shear modulus, Young's modulus, shear wave attenuation, shear elasticity, shear viscosity, mechanical relaxation time and anisotropy.

19. The imaging apparatus according to claim 18, wherein said apparatus is adapted to apply said with a bandwidth of at least 500 Hz and said electronic central unit is adapted to calculate said shear wave propagation parameter at a plurality of frequencies in said bandwidth.

\* \* \* \* \*